US008075496B2

(12) United States Patent
Deck et al.

(10) Patent No.: US 8,075,496 B2
(45) Date of Patent: Dec. 13, 2011

(54) INTEGRATED DEVICE FOR DIAGNOSTIC PURPOSES

(75) Inventors: Frank Deck, Niederkirchen (DE); Joachim Doepper, Darmstadt (DE); Christian Hoerauf, Oftersheim (DE); Rudolf Pachl, Ellerstadt (DE); Juergen Rasch-Menges, Schwetzingen (DE); Joerg Scherer, Zuchwil (CH); Guenther Schmelzeisen-Redeker, Lorsch (DE); Wilfried Schmid, Mannheim (DE); Jochen Schulat, Mannheim (DE); Bruno Thoes, Quierschied (DE); Sven Winheim, Leimen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1144 days.

(21) Appl. No.: 11/627,954

(22) Filed: Jan. 27, 2007

(65) Prior Publication Data
US 2007/0219572 A1   Sep. 20, 2007

Related U.S. Application Data

(63) Continuation of application No. PCT/EP2005/008135, filed on Jul. 27, 2005.

(30) Foreign Application Priority Data

Jul. 31, 2004   (DE) .......................... 10 2004 037 270

(51) Int. Cl.
    *A61B 5/00*   (2006.01)
(52) U.S. Cl. ....................................... 600/583
(58) Field of Classification Search .................. 600/583, 600/584; 606/181–183
    See application file for complete search history.

(56) References Cited

U.S. PATENT DOCUMENTS

| | | | |
|---|---|---|---|
| 5,464,418 | A | 11/1995 | Schraga |
| 5,797,942 | A | 8/1998 | Schraga |
| 6,190,398 | B1 | 2/2001 | Schraga |
| 6,210,420 | B1 | 4/2001 | Mauze et al. |
| 6,530,892 | B1 | 3/2003 | Kelly |
| 2002/0120216 | A1 | 8/2002 | Fritz et al. |
| 2004/0039303 | A1 | 2/2004 | Wurster et al. |
| 2004/0087990 | A1 | 5/2004 | Boecker et al. |
| 2004/0098009 | A1 | 5/2004 | Boecker et al. |
| 2004/0127819 | A1 | 7/2004 | Roe |
| 2004/0138588 | A1 | 7/2004 | Saikley et al. |
| 2005/0015020 | A1* | 1/2005 | LeVaughn et al. ............ 600/583 |
| 2006/0178600 | A1 | 8/2006 | Kennedy et al. |

FOREIGN PATENT DOCUMENTS

| | | |
|---|---|---|
| DE | 102 23 558 | 12/2003 |
| EP | 1 238 632 | 9/2002 |
| JP | 06-14889(B2) | 3/1994 |
| JP | 52001991(A) | 1/1997 |
| JP | 10127714(A) | 5/1998 |

(Continued)

*Primary Examiner* — Brian Szmal
(74) *Attorney, Agent, or Firm* — Bose McKinney & Evans LLP

(57) ABSTRACT

The present invention provides an integrated measuring device that includes a blood collection system for collecting blood for diagnostic purposes. The blood collection system comprises an electric motor which provides energy for propelling a lancet. The blood collection system comprises a mechanical energy store in which the electric energy that is converted by the motor is stored in the form of mechanical energy. The use of a mechanical energy store allows the use of known mechanical drive elements. The blood collection system can also be electrically activated and is thus easy to use for the operator. The motor can also be coupled to another system component, such as a test strip or lancet drum, to operate it.

39 Claims, 12 Drawing Sheets

FOREIGN PATENT DOCUMENTS

| | | |
|---|---|---|
| JP | 2001-214823 A | 8/2001 |
| JP | 2002-143132 A | 5/2002 |
| WO | WO 98/24366 | 6/1998 |
| WO | WO 02/078533 A2 | 10/2002 |
| WO | WO 02/000101 | 12/2002 |
| WO | WO 02/100251 | 12/2002 |
| WO | WO 02/100460 | 12/2002 |
| WO | WO 02/100461 | 12/2002 |
| WO | WO 03/070099 A1 | 8/2003 |
| WO | WO 03/071940 A1 | 9/2003 |
| WO | WO 2004/060143 | 7/2004 |
| WO | WO 2004/060162 | 7/2004 |

* cited by examiner

Fig. 2a
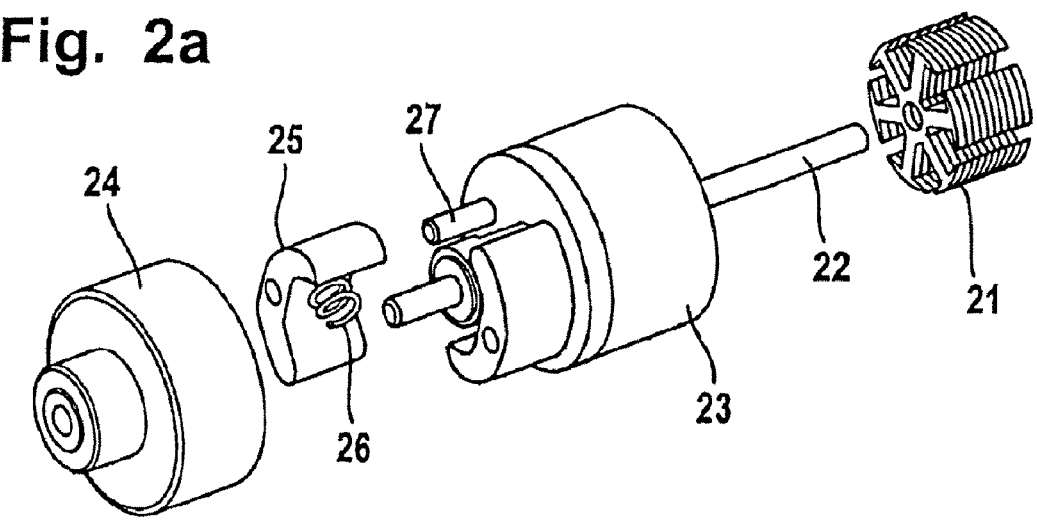
Fig. 2b
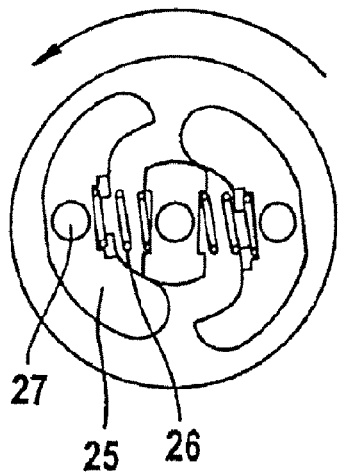
Fig. 2c
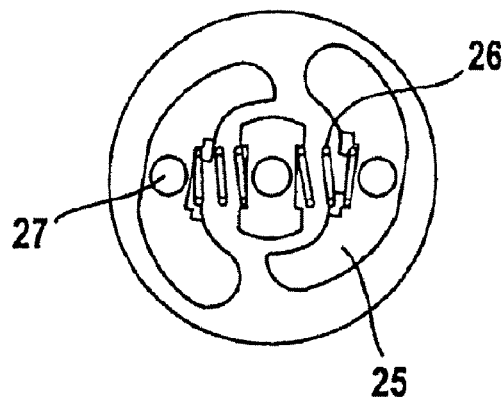
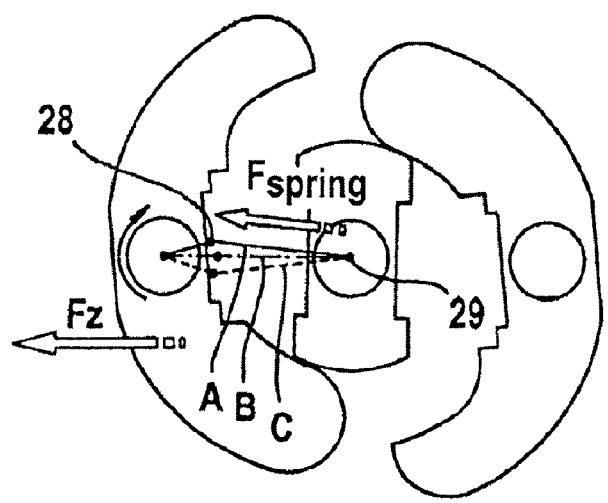
Fig. 2d

Fig. 4a
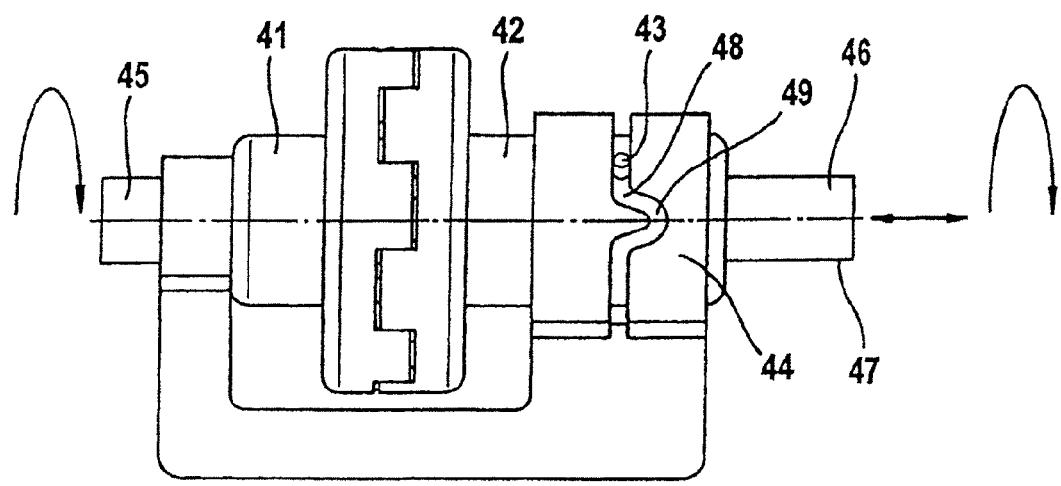
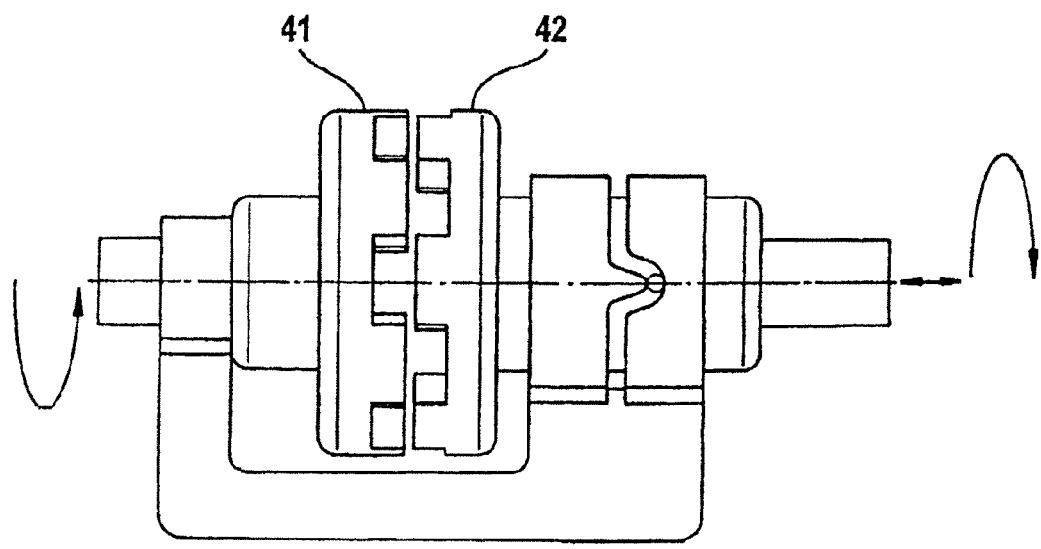
Fig. 4b

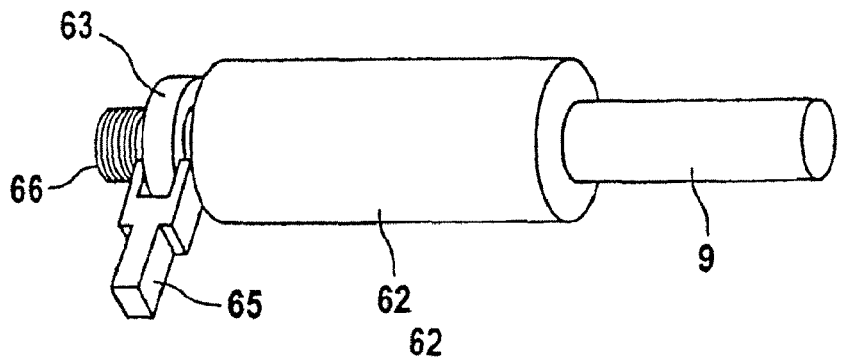
Fig. 7a
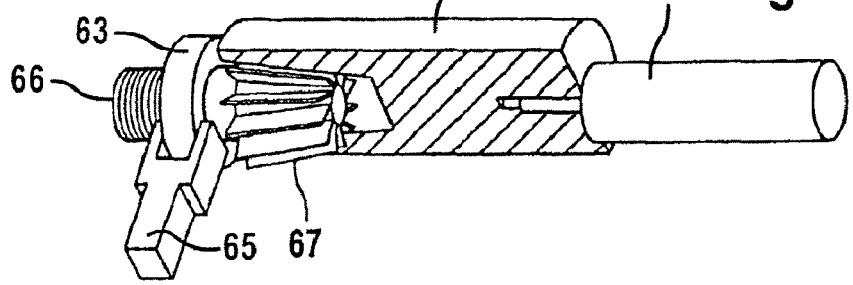
Fig. 7b
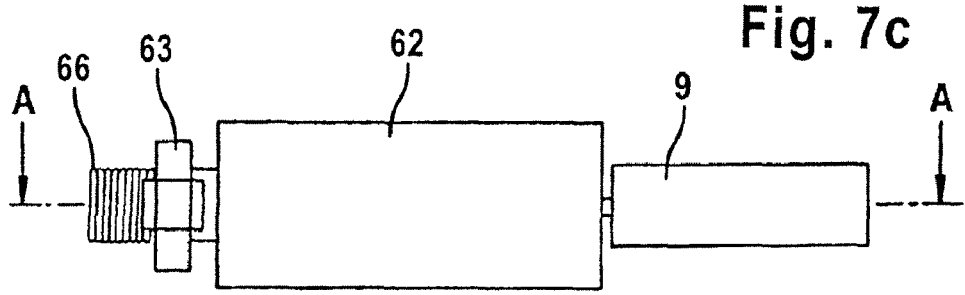
Fig. 7c
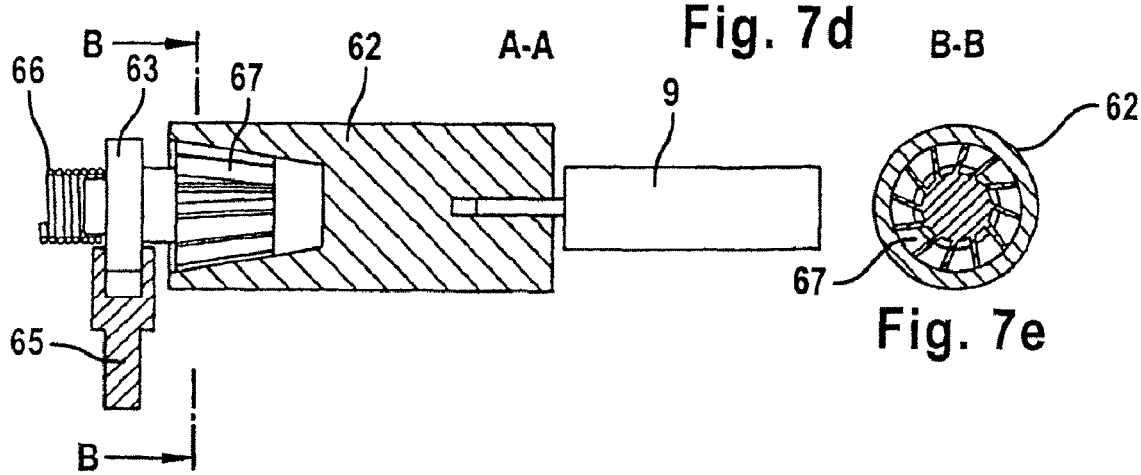
Fig. 7d
Fig. 7e A-A      Fig. 8d      B-B

INTEGRATED DEVICE FOR DIAGNOSTIC PURPOSES

RELATED APPLICATIONS

This is a continuation application of International Application PCT/EP2005/008135, filed Jul. 27, 2005, which claims priority to DE 10 2004 037 270.5, filed Jul. 31, 2004, which are hereby incorporated by reference in their entirety.

BACKGROUND

Lancets are used to lance an appropriate body part to generate a wound and collect blood from a body part (usually from the finger or the earlobe) for diagnostic purposes. Specially trained personnel are required if this is carried out manually. The puncture is nevertheless associated with considerable pain.

Blood collection systems have been used for a long time which are composed of a lancing device and associated lancets that are specially adapted to the respective device. A lancet drive which mechanically drives a lancet into the skin is located in a housing of the lancing device. A spring is usually used as the driving element for the lancing movement.

However, it is frequently necessary for a patient to be subjected several times daily to an examination in order to regularly monitor certain analytical blood values. This applies particularly to diabetics who must frequently check their blood sugar level in order to maintain it as constant as possible within certain required limits, which is accomplished by taking insulin injections as needed based upon the blood sugar level that is measured. Blood sugar levels may vary greatly depending on food intake, physical activity, etc.

Consequently, a prerequisite for this intensive therapy is that the blood collection cause as little pain as possible. Numerous different blood collection systems which comprise mechanical drive units for a lancet or needle have been developed with the aim of minimizing pain. Nowadays, such drive units are so highly developed that the lancing process can be carried out reproducibly in a relatively painless manner. However, before the blood collection system can be operated, a drive element, which is frequently a spring of the drive unit, must be transferred into a tensioned position. When the lancing process is subsequently triggered, the drive element is again transferred into a relaxed position. The energy which is released by the drive element in this process is used to drive the lancet in the lancing direction.

However, a disadvantage of the prior art is that the tensioning process of a blood collection system often requires significant force and/or complex handling steps by the user in the case of a blood collection system having a mechanical drive unit. For example, in the document DE 10223558.9, the tensioning of a blood collection system is described in which a spring is tensioned in the drive unit by turning a knob on the housing. This requires the patient to use both hands to operate the device.

Such handling steps are often perceived to be difficult by older persons or people with limited motor skills. Hence, in addition to a puncture that is as pain-free as possible, easy operation of the blood collection system is desirable, especially in the intensive therapy that is often required for elderly people.

Blood collection systems with an automatic drive have been described in the prior art which should enable simple and comfortable handling, especially for persons with motoric disabilities. The user is thus spared to the extent possible in some cases the complicated process of tensioning the lancets and the subsequent triggering of the lancing process. The patient can activate an electrical drive mechanism by pressing a button without additional handling steps or exerting force. The documents WO 02/100461, WO 02/100460 as well as WO 02/00101 and WO 02/100251 each disclose blood collection systems in which an electrical drive unit moves the lancet in the drive direction and executes a lancing process. For example, electromagnetic drive elements are mentioned in the document WO 02/100251. The transfer of force from the drive units to the lancet body is controlled by control units in such a manner that a defined lancing movement can take place.

An automatic blood collection system comprising a plurality of lancets is also disclosed in U.S. Pat. No. 6,530,892. The drive unit is realized by a magnet analogously to the above-mentioned prior art.

The systems described each utilize electrical drive units. A rapid transfer of force to the lancet, which converts the electrical energy into a movement of the lancet body, requires additional components. In order to achieve a high drive speed using electrical drive units, capacitors are typically integrated into an electrical drive unit and provide the energy required for lancing by a rapid discharge. This arrangement attempts to transfer the energy rapidly and directly from the electrical drive unit onto the lancet. Although electrical drive units are particularly suitable for use as a long-term store in lancing aids due to their high storage density of greater than 100 joules per gram, it has, however, been found that the rate at which energy can be removed from electrical drive units is usually limited to about 10 joule/sec due to a given internal resistance. Moreover, the efficiency of the system deteriorates as the rate of removal increases. Furthermore, additional measures are necessary to control a defined motion sequence of the lancet body in which the lancet pierces a body part of a patient in a vibration-free manner and the subsequent retraction of the lancet into the blood collection system is as desired.

Consequently, a disadvantage of the described prior art is that complicated control mechanisms which control a defined motion sequence of the lancet body during the lancing process are required in addition to the electrical drive units. Because of the presence of the electrical drive unit, it is not possible to integrate the already well-proven mechanical drive mechanisms into the system. Hence, one is not able to utilize the advantages of mechanical drive units which have been significantly improved in recent years and now enable a relatively painless lancing due to precisely defined sequences of motion.

Hence, complicated additional measures have to be implemented for electrical drives in order to control the lancing process in a manner comparable to that of mechanical drive units, and these measures still often prove inadequate in comparison to mechanical drive units. Furthermore, the additional components that are necessary for electrical drives, such as capacitors and control units, complicate the design of a lancing aid and thereby increase its manufacturing costs. Moreover, in addition to inadequate control of the motion sequence, the transfer of force from the drive unit to the lancet body is often delayed, resulting in a retarded motion sequence of the lancet body. This in turn increases pain from lancing. Hence, a comparison of electrical drive units with mechanical drive units shows that, although electrical drive units provide a higher storage density that is available to the system, the rate of removal and thus the force transfer of the drive unit onto the lancet body is often inadequate.

Thus, blood collection systems having an electrical drive unit present difficulties in satisfying the requirements of a relatively painless puncture.

In contrast, the use of a mechanical drive unit is defined by a high removal rate as is urgently required for a lancing movement of a lancet. Conventional springs provide a high removal rate of a few thousand joules per second at an almost ideal efficiency. However, mechanical drive units which are often in the form of a spring, prove inefficient as energy stores because they require large volumes for a high storage density. For example, compared to electrical drive units, a spring used in a typical mechanical drive unit has a low storage density of only about 150 mJ per gram. Consequently, in view of the compact designs of blood collection systems which are required in modern analytics, it is not possible to achieve a high storage density with a mechanical drive.

Furthermore, the use of mechanical drive units often necessitates a complicated handling by the user that requires much force which, as already discussed above, is regarded as disadvantageous.

Hence, it has become increasingly apparent in recent years that there is a great interest in a blood collection system which simultaneously fulfills the difficult and partly contrary requirements of minimal pain sensation, simple operation, compact, slimmest possible design, and as simple and economical a construction as is possible.

SUMMARY OF INVENTION

Embodiments incorporating the present invention address the disadvantages described of the prior art and provide a blood collection system which allows simple handling, especially for elderly or disabled persons, which also provides a relatively painless puncture for blood collection. In particular, the tensioning of a blood collection system which is often complicated and involves much force from the user is simplified.

One embodiment comprises a lancing aid to generate a skin opening in a body part. The housing of the lancing aid has an opening from which a lancet can emerge. A lancet which is driven by a drive unit to execute a lancing process is positioned within the housing. The drive unit of the blood collection system comprises a mechanical energy store that can be connected via a motor with an electrical energy store such that energy can be provided to propel the lancet. As already described, an electrical energy store is characterized by a high storage density and can, for example, contain batteries or rechargeable batteries. In order to remove energy from the electrical energy store, a motor is coupled to the electrical as well as to the mechanical energy store such that the electrical energy provided to the motor can be converted into mechanical energy and stored. In contrast, the mechanical energy store is characterized by a rapid removal rate and provides the system with the energy required to execute a lancing process within a few milliseconds. The lancet body is coupled to the mechanical energy store by means of a coupling mechanism such that the stored energy can be transferred directly and immediately to the lancet body. In an exemplary embodiment, the coupling mechanism between the mechanical energy store and lancet comprises a mechanical motion transducer to control the sequence of motion of the lancet body, such that the lancet executes a positively guided movement. The lancet movement in or opposite to the lancing direction can thus be controlled in such a manner that it ensures a relatively painless puncture.

The system enables an electric motor to be combined with a mechanical energy store and thus with other mechanical components of a drive unit of a blood collection system, thus ensuring a controlled motion sequence of the lancet body during the lancing. Thus, the system can utilize known principles of mechanical components such as control guide blocks (see, for example, U.S. Pat. No. 6,409,740 and U.S. Pat. No. 6,419,661) that are used to couple a spring to a lancet in order to couple the lancet body to the mechanical energy store. In this manner, components that have already been well-tested in recent years can be integrated into the system in order to guide the lancet body in a mechanical drive in a defined manner. Complicated control units such as those required for electrical drives are unnecessary. Moreover, the system has both a high storage density and a high removal rate. Consequently, the blood collection system according to the exemplary embodiments is characterized by a combination of an electric motor and a mechanical energy store in which electrical energy can be converted into mechanical energy.

A mechanical energy store can be realized in a variety of embodiments. The mechanical energy store is advantageously integrated into the drive unit as a solid body. Such an energy store is, for example, a spring such as those that are already used for mechanical drive units. The spring is then tensioned by an electric motor which first compresses the spring. A spiral spring, torsion spring or leg spring, etc., such as those that are already known in the art can, for example, be used as a spring. The lancing process can then be triggered by releasing the spring. As for mechanical drive units, an appropriate coupling mechanism between the spring and the lancet body can be used.

In order to tension the spring, it may be helpful for the motor to be coupled to the mechanical energy store by means of a clutch and/or gear unit. In this manner, the torque required to tension the spring can easily be provided even by relatively small motors.

If a clutch is used as a connection between the motor and mechanical energy store, torques of 30 mNm can thus be transferred to the mechanical energy store in a simple manner. In certain embodiments, the clutch may transfer torque of at least 10 mNm to the mechanical energy store. Torque-controlled or angle of rotation-controlled clutches which at the same time allow a simple control of the motor are advantageous as a clutch between the motor and mechanical energy store. Bevel gearing can be used as a gear unit. Other types of gearing or couplings that are already known in the art which enable a coupling of the motor to the mechanical energy store are also conceivable.

If a clutch is used to transfer the force of the motor to the mechanical energy store, it is, as described above, conceivable that the motor can be controlled on the basis of the applied torque. In this event, in an advantageous embodiment the motor current is measured during the tensioning process and compared with preset values. If, for example, a spring is used as the mechanical energy store, the torque required to tension the spring increases with an increasing compression of the spring. Consequently, the motor current increases as a function of the compression of the spring, such that each measured value of the motor current corresponds to a defined compressed state of the spring. Hence, a preset value for the motor current can be used to signal the system that the tensioning process has been completely executed. If the motor current exceeds such a threshold value, the motor is stopped to end the tensioning process of the spring. Hence, the motor is automatically controlled in a simple manner. The described advantageous embodiment allows a propulsion of the blood collection system without needing additional positioning sensors to control the operating sequence. The lancing process can subsequently be triggered in the same manner by a control based on the applied torque. In this event, the motor is first activated again so that the tensioning process of the spring is initially continued until a second preset torque, i.e., a second threshold, is reached. Once the preset torque of the second threshold is reached, the connection between the motor and the spring is automatically released so that the mechanical energy stored by the spring can be released. The spring relaxes, as a result of which the lancet body is propelled by the energy released by the spring. In this connection, the energy can act in a defined manner on the lancet body by means of appropriate coupling mechanisms to transfer force between a spring and lancet body.

An analogous control of the motor by other embodiments is also conceivable in which, for example, the coupling is controlled by means of the angle of rotation.

Furthermore, a mechanical energy store in the form of a solid body can also be realized by a mass which is rotated by a motor. The kinetic energy generated in this manner is transferred to the lancet body such that the lancet executes a puncturing movement. This illustrates that the electrical energy of the motor can be converted to potential as well as kinetic energy and can be stored by a mechanical energy store. If the electrical energy is stored by the mechanical energy store as kinetic energy, the lancet body must also in this case be subsequently coupled to the mechanical energy store such that the stored energy can be released directly without loss and converted into a targeted movement of the lancet body. When a rotating mass is used as the energy store, a clutch is advantageously provided as a coupling mechanism between the mechanical energy store and lancet body which allows the kinetic energy of the mass to in turn act on the lancet body or, in a preferred embodiment, on a mechanical motion converter. Such a coupling can comprise a frictional directional lock and a shaft as are well-known in the prior art. Embodiments comprising a coil spring or an automatic clutch, as described in detail in the following description, are also conceivable. The integration of the clutch between the moving mass and the lancet body enables the energy to be removed at a high rate and thus achieves a coupling time preferably in the range of 1 ms.

Hence, in addition to the embodiments for coupling the spring to the lancet body that are already known in the prior art, it is also possible to use clutches as a coupling mechanism between a mechanical energy store and lancet body which allow a direct transfer of energy from a moving mass to the lancet body. The mechanical energy store and lancet body can thus be coupled by simple mechanisms that are, for example, described for mechanical drive units in U.S. Pat. No. 5,318, 584. On the other hand, it is also advantageous to use clutches and/or gear units. In this case, the component that is responsible for the coupling between the mechanical energy store and lancet body can also at the same time act as a mechanical motion converter or in turn be connected to the lancet body by means of a mechanical motion converter such that the lancet executes a positively guided movement. Examples of this are a cross-sliding gear unit which enables the components to be coupled and also acts as a mechanical motion converter.

The embodiments discussed are only given as examples. Other embodiments for transferring energy are also conceivable as is a combination of these embodiments with the mechanical energy stores known in the art.

Mechanisms such as those used in the art for mechanical drive units can also be used as mechanical motion converters to guide the propelled lancet body in a defined manner. The principle of a controlled link (DE 10223558.9) is mentioned in this regard. In this case, a control guide block enables a defined motion sequence of the lancet body in and opposite to the direction of lancing. However, it is also possible to use gear units e.g. cross-sliding gear units as described above.

The system in exemplary embodiments allows an electric motor to be integrated into conventional mechanical drive units of blood collection systems. In this manner it is possible to fulfill the simultaneous demands of painless puncturing and ensuring a comfortable handling, especially for patients with motoric limitations.

The system according to exemplary embodiments allows a simple and economic design. A motor is coupled to a mechanical drive element that is already in the art. This is achieved in particular by converting electrical energy into mechanical energy by means of a motor. Use of a mechanical energy store allows the coupling to further mechanical components such as a mechanical motion converter such as are used for a defined guidance of the lancing movement in mechanical drive units. This results in a high removal rate as well as a defined motion sequence.

Electric motors (DC motors, external rotor motors or brushless motors) or a so-called "memory shaped alloy actuator" can be used as the motor. In the case of the so-called "memory shaped alloy actuator," which is also referred to in the art as "nanomuscle," individual elements consisting of extremely pure alloys are heated by a current which results in a change in their shape, i.e., an expansion of the respective elements. In certain embodiments, the motor may comprise a piezoelectric motor or an external rotor motor.

The system according to exemplary embodiments also proves to be particularly advantageous for use in integrated systems which advantageously combine several functions in one analytical system. Such systems save the user complex handling steps by integrating several system functions in one device. Thus, the use of integrated systems enables the user to, among other things, first carry out a lancing process and subsequently to apply the blood to a test element provided by the system using a single device. The test element is then analyzed directly in the instrument without the patient having to switch between different elements of the device, such as lancing aids, test elements, and measuring instruments. For example, integrating of a lancing aid in a measuring instrument is described in the document WO 98/24366. These integrated systems enable the patient to carry out all handling steps necessary for the analysis by one device. However, systems are also known which have different types of integration.

Examples of less complex instruments, in which the lancing aid is handled separately from the measuring instrument, have a store of test elements as well as an automatic dispensing of test elements. Examples of this are the AccuCheck Compact® instrument from Roche Diagnostics GmbH. Such integrated systems can also advantageously have a lancet magazine in addition to a test element magazine. If a system according to the invention is combined as described with an integrated system, this would fulfill the high requirements for comfortable handling.

When integrating the system, the electric motor can then be used as a combined drive in an advantageous embodiment. With a combined drive, the electrically-driven motor, on the one hand, provides energy for the mechanical energy store and, on the other hand, the electrically driven motor can at the same time, or at a time that is independent thereof, provide energy for another system function. This system function can be magazine transport, test element transport, etc.

If the motor is used successively for different functions, it proves advantageous to employ an additional gear unit and/or clutch which couples or uncouples the motor to the corresponding system function. In this manner, the motor can be used for the respective system functions in a spatially as well as chronologically independent manner. A compact design of highly integrated systems is thus possible.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein:

FIGS. 2a-2d are various views of a rotating mass used as a mechanical energy store with an automatic clutch;

FIGS. 4a and 4b are plan views of a system with a clutch controlled by angle of rotation;

FIGS. 7a-7e are various views of a second embodiment of a system with a rotating mass used as a mechanical energy store; and FIGS. 8a-8e are various views of yet another embodiment of a system using a rotating mass as a mechanical energy store.

Corresponding reference numerals are used to indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1A:
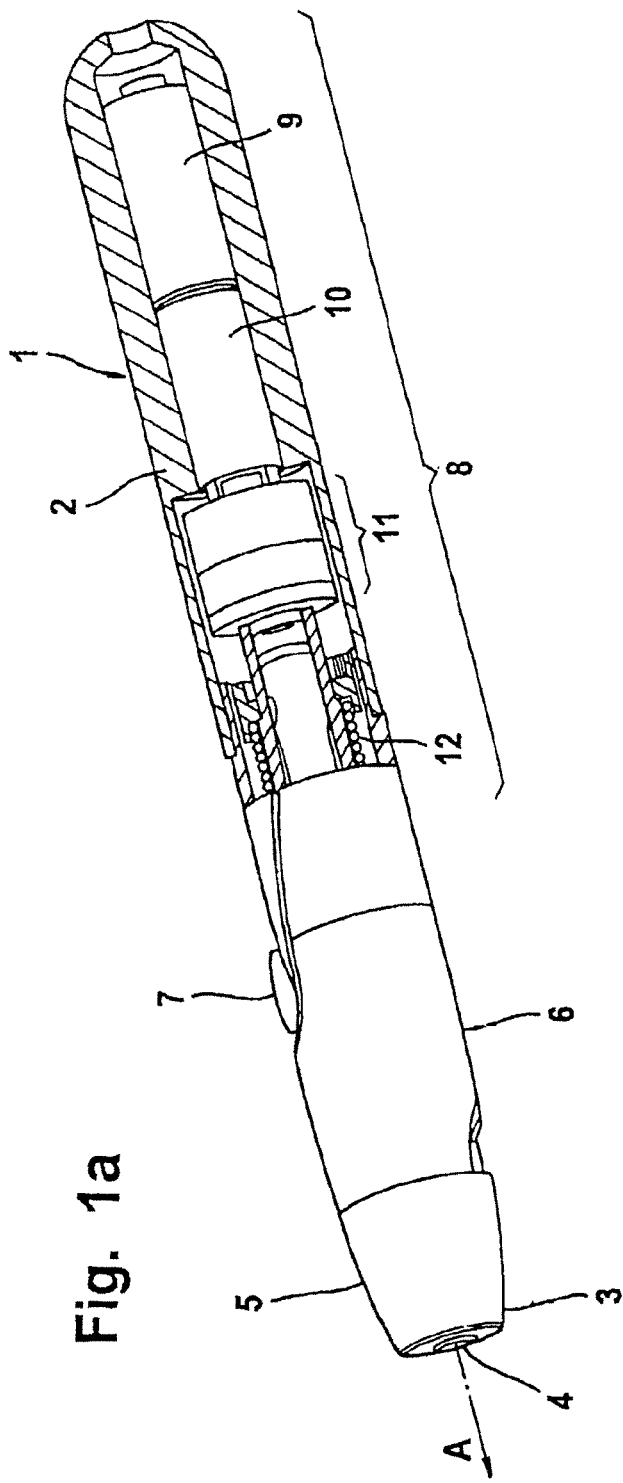
FIG. 1a is a perspective view in partial cross-section of an electric lancing aid using a spring as a mechanical energy store.

FIG. 1a shows a transverse section through a blood collection device 1. The device comprises an outer housing 2, the front end of which 3 has an exit opening 4 for a lancet tip. The exit opening 4 is integrated into a cap 5 of the lancing aid which is rotatably connected to the housing 1. The extent to which a needle tip emerges from the opening 4 can be changed by rotating the cap 5 about the axis A and thus the puncture depth of the blood collection device can be selected by the user. In addition, a lancet and preferably a lancet magazine (not shown) from which lancets are removed for the lancing process can be arranged in the front area 6 of the blood collection device. In order to perform the lancing process, the lancet is propelled by a drive unit 8 in the direction of lancing along the axis A and is retracted again into the housing after the lancing process. In the example shown, the drive unit comprises a motor 9 which is connected to a store of electric energy in the form of a battery (not shown). The electric motor is coupled by a gear unit 10 to a clutch 11. If the motor is activated by the user to execute a lancing process, a rotational movement is transferred via the gear unit and clutch to the spring 12, which is thus compressed. In this process, the clutch generates the torque required to compress the spring such that the spring can be adequately compressed even when the motor has a low power. The motor is advantageously controlled by measuring the applied motor current and thus the prevailing torque. If this exceeds a predetermined limit, it serves as a signal to the system that the spring is adequately pretensioned and the motor is then automatically stopped. The user can then trigger the lancing process by a trigger button 7. In this process, the user again activates the motor by actuating the trigger button, as a result of which the spring is again compressed until a second predetermined torque is reached. When the second limit is reached, the spring which was previously locked in a tensioned state is automatically released such that the potential energy stored by the spring can be released. The released energy of the spring is now diverted by a motion converter (not shown), e.g., a control guide block onto the lancet body such that the lancet executes a positively guided movement and a painless insertion into a part of the body can be performed.

Figure 1B:
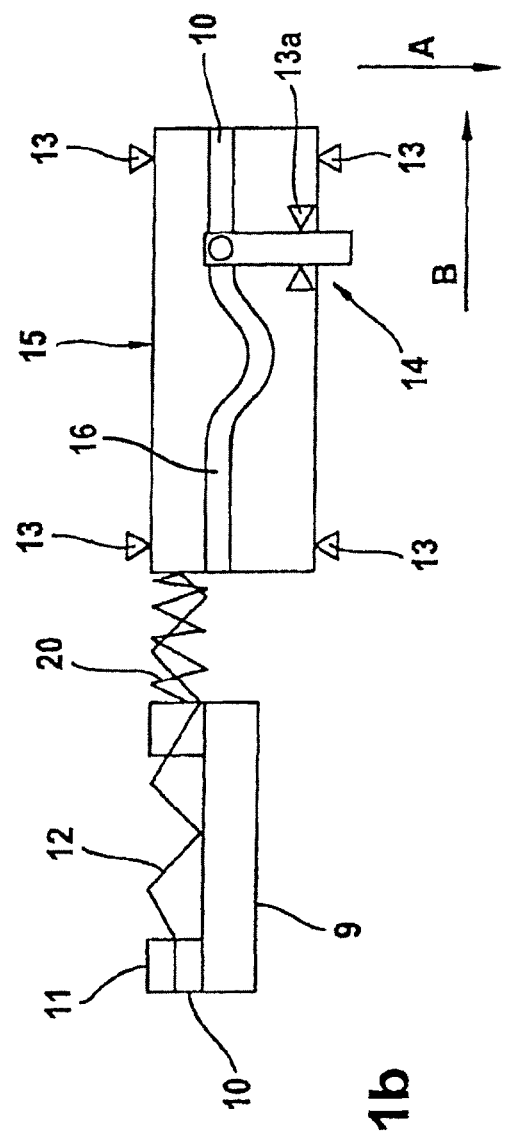
FIG. 1b is a schematic view of an electric lancing aid with bevel gearing and spring.

FIG. 1b shows a rough functional model of an automated lancing aid which illustrates the coupling of the motor to a mechanical energy store and to a mechanical motion converter which guides the lancing movement of the lancet body. In the example shown, the motor 9 is only shown schematically and is coupled by a gear unit 10 and a clutch 11 to a spring 20 as a mechanical energy store. The second end of the spring is connected to a guide block 15 which is movably supported by the bearings 13. The guide block has a guide slot 16 which serves as a control guide block for the lancet holder 14, which is movably supported by bearings 13a. If the motor is activated to tension the spring, the spring is compressed and the guide block is moved towards the motor. Hence, the guide block can be moved laterally relative to the motor. In contrast, the lancet holder 14 has a fixed position in the system along the direction B and remains fixed in its lateral position relative to the motor while the guide block is moved laterally. Meanwhile, the lancet holder is guided along the guide slot or control curve 16, which causes the lancet holder to be deflected perpendicularly to the movement of the guide block. Consequently, the lancet holder makes a movement or stroke along the lancing direction A and is subsequently returned to its original position by the design of the guide slot. After the tensioning, the position of the guide block is locked in the system. When the lancing process is triggered, the arrestment is first released so that the spring can again return to its tensioned state. Due to the resulting movement of the guide block perpendicular to the lancing direction A, the lancet holder 14 again passes through the guide slot 16 which executes the lancing process.

Figure 1C:
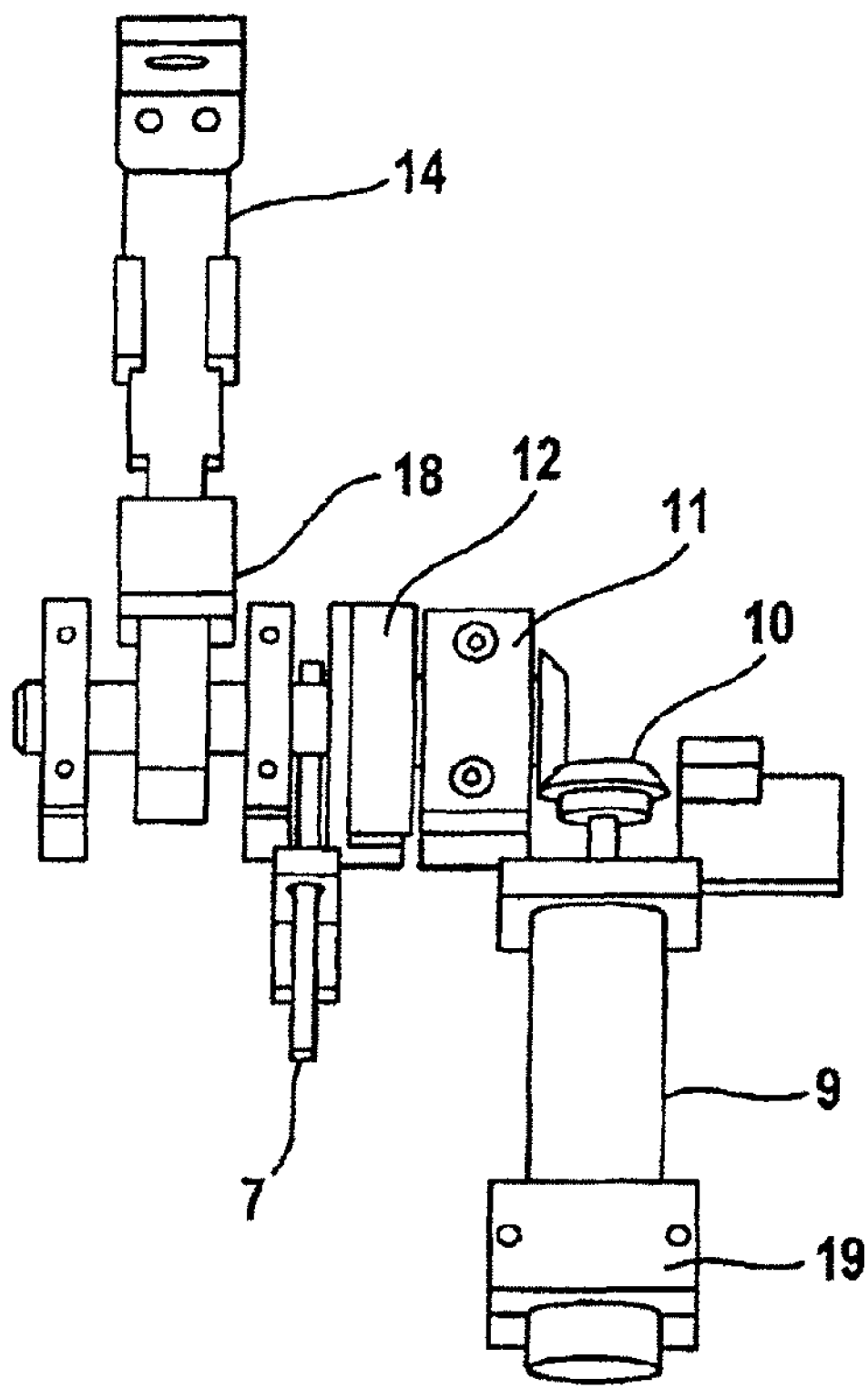
FIG. 1c is a perspective view of an electric lancing aid with a movably guided guide block.

FIG. 1c shows a system according to the invention with a cross slip gear unit as a mechanical motion converter. The system has an electrically driven motor 9 which is fixed in position in the system by a bearing 19. The motor is connected to a bevel gear 10 which is in turn connected to a clutch 11 (only indicated schematically). The conical gear enables a flexible design of the spatial structure of the system such that the motor, as shown in the figure as an example, does not have to be located linearly behind the lancet holder 14. Thus, the energy provided by the motor can be readily deflected by 90°.

This enables a compact design of the system. It is also possible to integrate other system functions (not shown here) in which case the spatial structure of the system according to exemplary embodiments can be adapted according to the other system functions. If the bevel gear and the clutch are driven by the motor, a spiral spring 12 is tensioned. In the described example the motor is controlled according to the angle of rotation and the motor is stopped as soon as the clutch has rotated by 360°. The spring is locked in its tensioned state. The blood collection system is now ready for operation. The spring is released by actuating a trigger switch 7 and the stored potential energy is transferred to the lancet body by a cross slip gear unit 18. In the example shown, a cross slip gear unit is used as a mechanical motion converter, which causes a positively guided movement of the lancet holder. The described embodiment shows an example of a combination of various possible constructional elements of a system according to one embodiment. It is also conceivable that instead of a cross slip gear unit, a control guide block as described in FIG. 1b is integrated into the system. In this connection a versatile combination of the individual constructional elements allows a flexible design which can be adapted according to the requirements especially for integrated systems.

FIGS. 2a-2d show a detailed view of a drive in which a rotating mass is used as the mechanical energy store. Such a system is essentially designed like the blood collection device shown in FIG. 1. However, instead of the mechanical energy store which is shown by a spring in FIG. 1, a rotating mass is used in this case. This results in some adaptations in the system to enable a rapid and efficient energy transfer of the rotating mass onto the lancet body. In the following only the detailed view will be shown for the system components which enable a direct transfer of energy from a rotating mass onto a lancet body. In this connection, FIGS. 2a-2d illustrate the function of an automatic clutch which transfers the kinetic energy directly onto a lancet body or, on the other hand, is first coupled to a spring such that a clutch is indirectly coupled to the lancet body by means of a spring. If the clutch is connected to a spring, the kinetic energy is first converted into potential energy which is first stored temporarily in the spring. An abrupt coupling of the automatic clutch transfers sufficient energy from the rotating mass to the spring in order to tension the spring. Of course, the automatic clutch can also be directly connected to the lancet body. The advantages and disadvantages of these system variants are as described below in FIG. 6. Furthermore, similarly to the system shown in FIG. 1, the constructional elements are coupled to a motor, lancet body, etc., which are not shown here in order to simplify the illustration.

FIG. 2a shows an exploded view of a drive with a rotating mass as well as an automatic clutch. A brushless external rotor motor is used as the drive. It includes a bank of stator plates 21 on which coils are applied (not shown), a soft iron rotor 23 with incorporated magnets and a common spindle 22. An automatic clutch consisting of the constructional elements 24-27 is permanently connected to the rotor 23. A clutch housing 24 is, as described above, either directly connected to a lancing gear unit to be driven or is axially connected to it by means of a spring (not shown). The bank of stator plates 21 and the spindle 22 are fixed in position (non-rotating) in the system. When it is switched on, the rotor 23 rotates and the clutch elements 25-27 that are permanently connected to the rotor follow the sequence of movements and rotate about the stator 21. The clutch housing 24 is pivoted on the common spindle 22 and is not connected to the constructional elements 23, 25, 26, 27 such that the clutch housing first remains stationary in the system. Above a threshold revolution speed the rotating constructional elements of the automatic clutch are abruptly coupled to the clutch housing 24. The stored energy of rotation of the rotor as well as of the rotating constructional elements is thus transferred into the clutch housing and the lancing gear unit that is connected thereto or a spring. The motor is blocked after the coupling process and is switched off by control electronics. The automatic clutch subsequently automatically separates the connection between the rotor 23 and the clutch housing 24. The system is ready for a new operation.

The detailed mode of operation of the automatic clutch is shown in FIGS. 2b-2d. FIG. 2b shows the clutch in an uncoupled state, below the threshold rotation speed. The two symmetrically disposed coupling jaws 25 are held in a resting position by the springs 26. The surfaces of the coupling jaws 25 have no contact with the surrounding clutch housing. When the rotation speed threshold is exceeded, the coupling jaws 25 rotate about the bearing pins 27 and touch the clutch housing. The clutch is coupled into the clutch housing 24 by frictional coupling of the jaws 25 with the inner wall of the housing such that the clutch housing follows the rotational movement. In order to avoid frictional losses during the coupling process, this must occur as suddenly as possible. For this purpose a special spring arrangement 26 is selected as a sprung mechanism as elucidated in the following. The position of the spring during the coupling process is shown schematically in FIG. 2d by the lines A-C. Line A symbolizes the initial position (not coupled) of the clutch whereas line C shows the final position of the spring above the rotation speed threshold. The spring is attached in the system between points 28 and 29 and acts as a pressure spring. Due to the position of the centre of mass of the coupling jaws outside of the pivot bearing, a centrifugal force $F_z$ is generated during rotation which is proportional to the rotation speed. As a result of the chosen arrangement the spring is compressed with an increasing centrifugal force $F_z$. The maximum of compression is achieved at the rotation speed threshold and is symbolized by the line B. However, this state is unstable and leads directly and suddenly to a further rotation of the jaws into the position corresponding to line C. As soon as the rotor is stopped, the clutch housing is decoupled. Stopping the motor reduces the centrifugal force $F_z$ to zero and due to the spring force $F_{spring}$, the coupling jaws are rotated back into the uncoupled initial position. The described embodiment of an automatic clutch ensures that by means of the coupling of the clutch housing the energy can be directly transferred suddenly onto the lancet holder in a direct or indirect manner. This enables the energy to be removed at a sufficiently rapid rate so that a lancing process of the lancing body can be carried out in a painless manner or so that a spring can be tensioned as a temporary store.

Figure 3A:
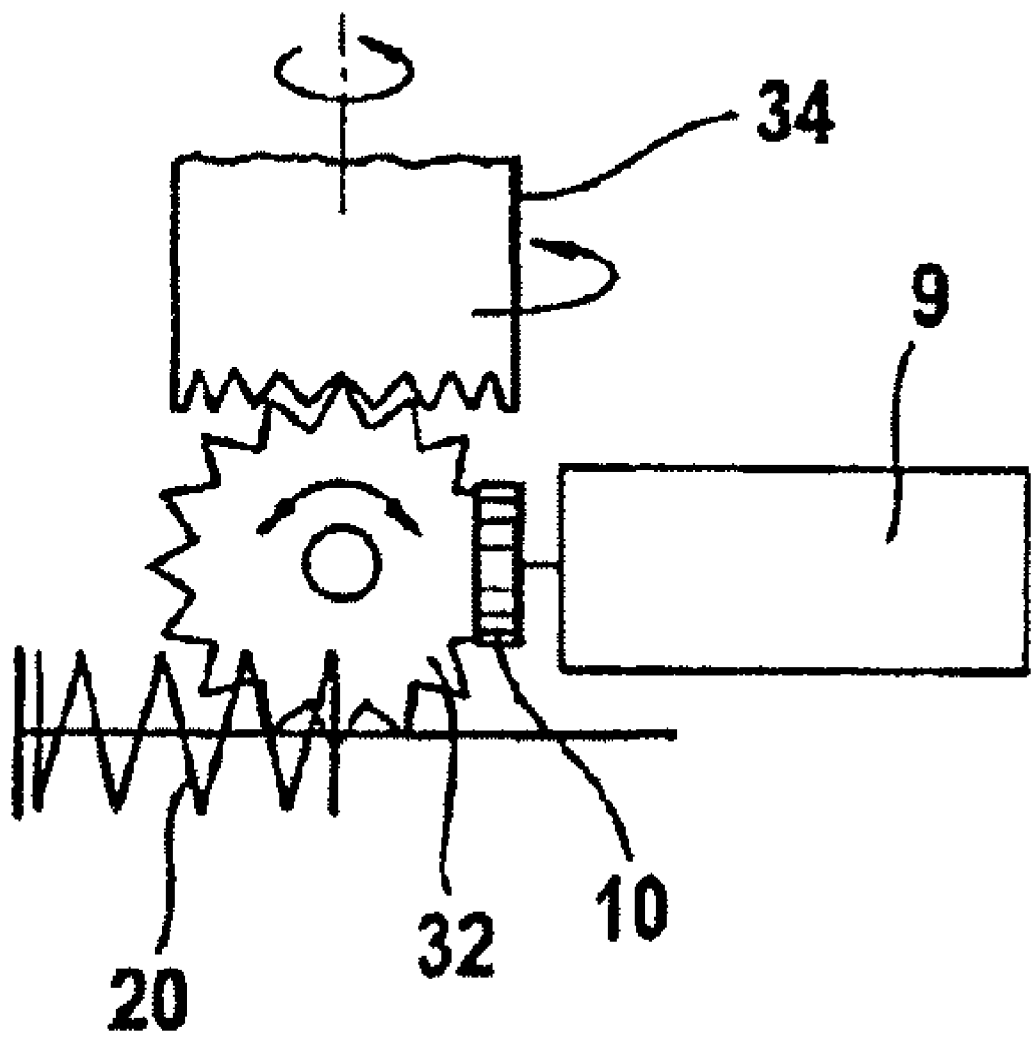
FIG. 3a is a schematic view of an integrated system with a combined drive.

FIG. 3a shows schematically a possible design of a combined drive ("combidrive"). A combidrive enables a further miniaturization and a reduction of the weight of the device for integrated systems. The user is thus ensured a comfortable handling with a compact portable device. Furthermore, operating errors of the system are reduced. In this connection the motor 9 is connected via a gear unit 10 to a gear wheel 32 which is pivoted in the system. The gear wheel can rotate in different directions by setting the motor in motion. In the example shown the gear wheel is coupled to a spring 20 to store mechanical energy and is also directly coupled to one side of the housing of a drum magazine 34. Hence, the motor is coupled by a gear unit 10 to two system functions or components. Rotation of the gear wheel results in compression of the spring 20. On the other hand, the gear wheel engages an appropriately designed base of the drum magazine such that the magazine is rotated about its longitudinal axis. The magazine can be provided to store test strips or lancets, and the magazine is thus rotated in such a manner that a disposable in the magazine is positioned opposite to a removal unit in the device. Thus, it is conceivable that during the tensioning of the spring to propel a lancet, the drum is at the same time advanced by one step such that a test strip can be removed from the magazine for sample application by means of a withdrawal unit provided for this purpose, such as a plunger.

Figure 3B:
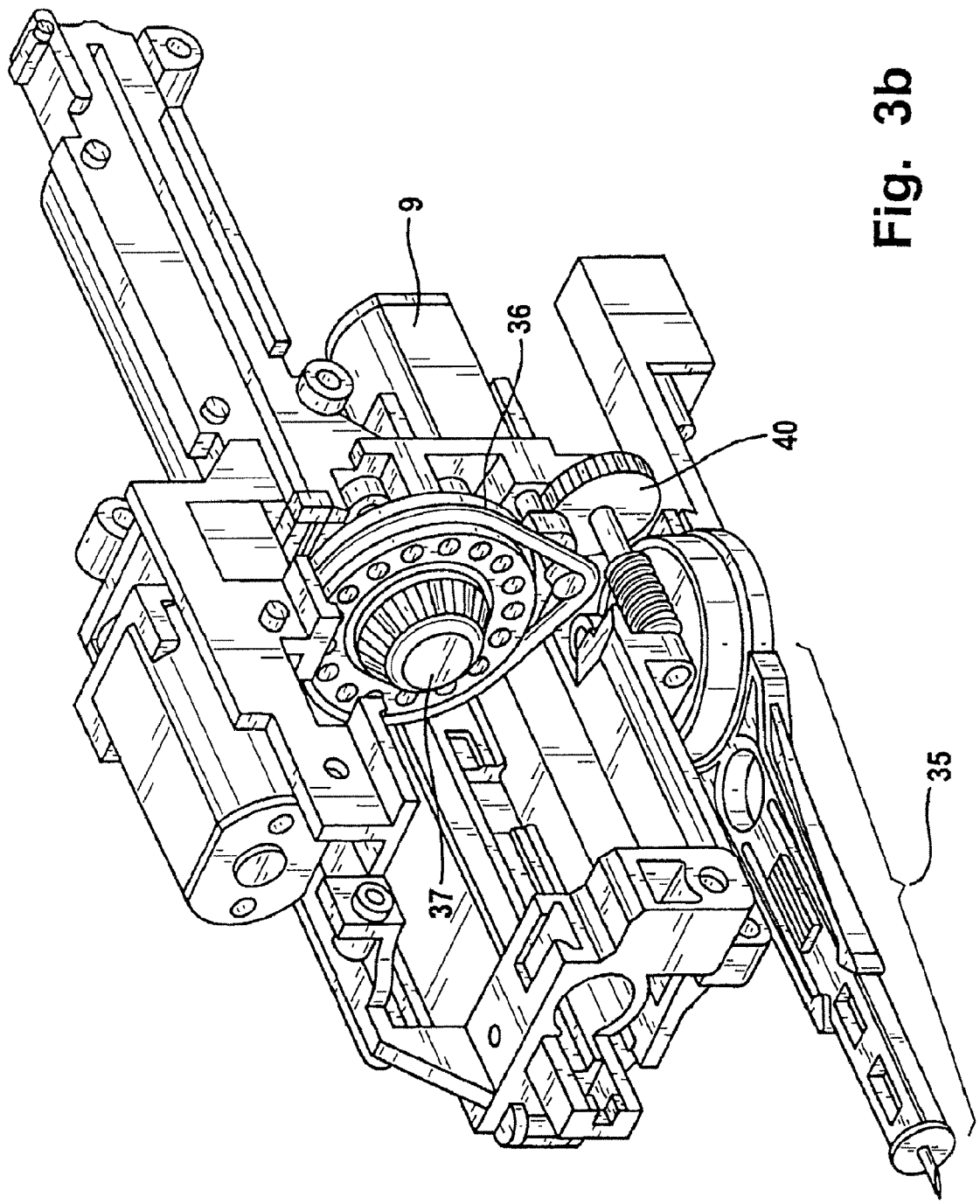
FIG. 3b is a perspective view of the integrated system of FIG. 3a shown with a combined drive for a drum magazine.
Figure 3C:
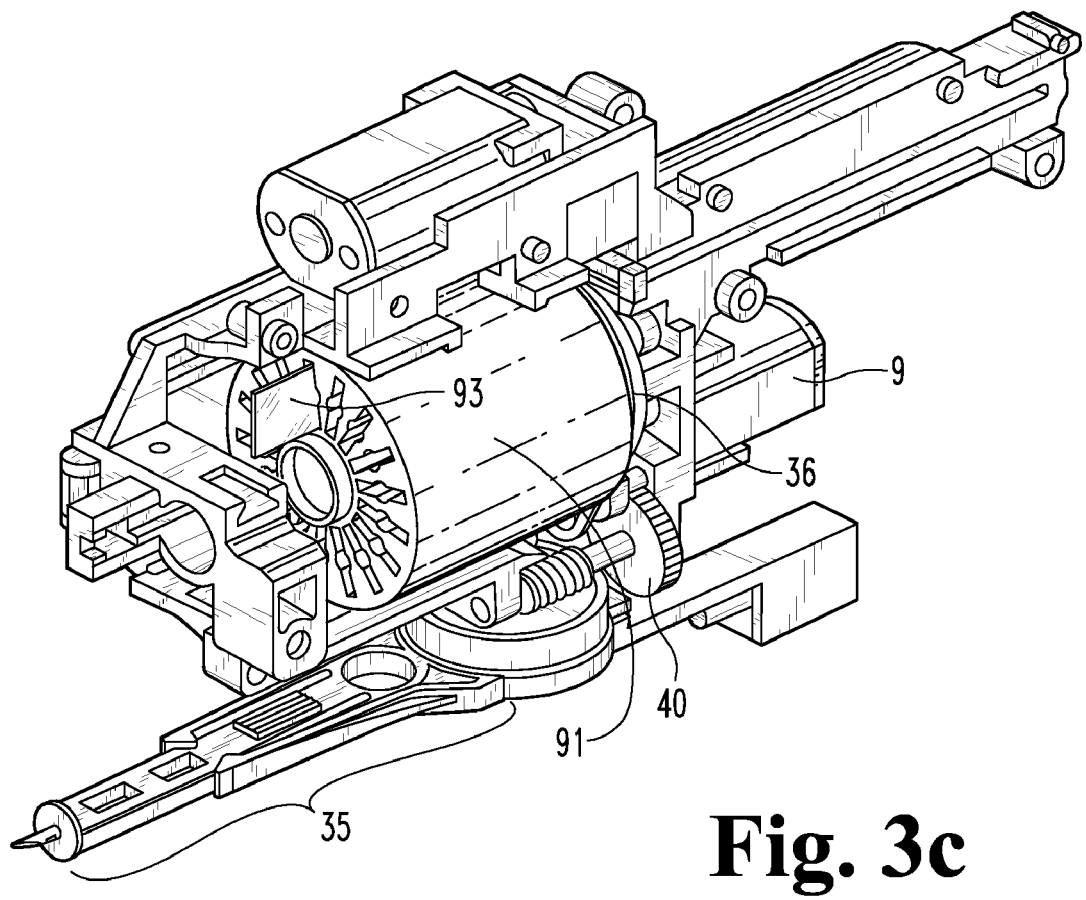
FIG. 3c is a perspective view of the integrated system of FIG. 3b and shows in addition a drum magazine with test strips therein.

FIG. 3b shows a detailed view of the combidrive shown in FIG. 3a which serves as a magazine transporter and is also used to tension a spring to propel a lancet. The combidrive consists of a DC motor 9 which at the same time advances a drum magazine in steps and tensions a lancing aid 35. A drum magazine 91 having test strips 93 is shown in FIG. 3c. The motor is connected with a gear unit 36 to drive the drum. The gear unit diverts the electric energy provided by the motor onto a spindle 37 which is made to rotate. The upper head of the spindle has a tooth-like structure which engages in a correspondingly shaped housing base of a drum magazine (not shown). Thus, when the drum magazine is inserted into the measuring device, it is placed on the spindle 37 and is arrested there. If the motor is activated and the spindle is rotated, the drum follows the movement. In order to also tap off energy to tension the lancing aid, a spur gear 40 is also connected to the gear unit 36. Hence, in the example shown the magazine is advanced by one step while at the same time the spring of the blood collection system is tensioned. The user can now trigger a lancing process as desired and request the output of one new test element from the magazine. It is of course possible to chronologically separate the system functions (tensioning of the spring and advancing the magazine) from one another. Under these circumstances the system advantageously comprises a clutch which uncouples and couples a system function from the motor provided an activation of the respective system function is desired. The lancing aid can be designed with a spiral spring, as is used in the example shown, as a mechanical energy store. With regard to the further design of the lancing aid, reference is made here to the systems that are already known in the prior art, for example, U.S. Publication No. 2005/0090850, which is incorporated by reference in its entirety.

In principle, a combidrive could be used for any system functions and is not limited to particular applications. A test element transport is mentioned here as an example. Another example would be a transport which advances a test tape rather than a magazine.

FIGS. 4a and 4b show a detailed view of a coupling controlled by the angle of rotation as it is used to couple the electric motor to a spring. A first spindle region 45 of a spindle 47 of the clutch is contacted with a spring (not shown) of a lancing aid while a second spindle region 46 of the spindle is connected to an electric motor (not shown) and is driven by this motor. For this purpose the spindle region 46 is inserted into an interface of the motor (not shown) and is turned by this motor. The end of the spindle region 46 that is not connected to the motor has a toothed structure 42 which engages in the toothed structure of the opposite end 41 of the spindle region 45. The rotation-secure intermeshing of the two spindle ends ensures that a rotary movement of the spindle region 46 caused by the motor is transferred onto the spindle region 45. Hence, a rotation of the spindle region 46 results in a rotary movement of the entire spindle 47. Thus, a spring (not shown) that is permanently connected to the spindle region 45 is compressed and thus tensioned as a result of the rotation of the spindle. The coupling additionally has a guide block 44 in which the first spindle region 46 is guided by a bolt 43 which is permanently connected to the spindle region 46. If the spindle region 46 is rotated, the bolt 43 is guided correspondingly along the guide block 44. As a result, the bolt 43 and the spindle region 46 that is permanently connected thereto are axially deflected according to the contour of the guide block. As a result of the axial displacement of the spindle region 46, the toothed structures 41 and 42 are uncoupled such that the spindle regions 45 and 46 are detached from one another. The torque caused by the compression of the spring now results in a rotation of the spindle region 45 in the opposite direction so that the spring drive can run back in an almost frictionless manner. The energy released in this process is transferred onto the lancet body such that the lancet body is moved in the direction of lancing. Thus, FIGS. 4a and 4b show a clutch which allows a control of the motor and thus of the drive unit as a function of a specified angle of rotation which is predetermined by the contour of the guide block. By turning the spindle 47, the bolt 43 of the spindle region 46 first reaches a position 48 of the guide block. In this position, the spindle region 46 is subjected to a first axial deflection which stops the motor. In order to trigger the lancing, the motor is again activated by the user. As the angle of twist increases, the bolt 43 continues to follow the forced guidance by the guide block until it reaches the position 49. As a result, the spindle region 46 is deflected to such an extent that the spindle ends are uncoupled as described above.

Figure 5A:
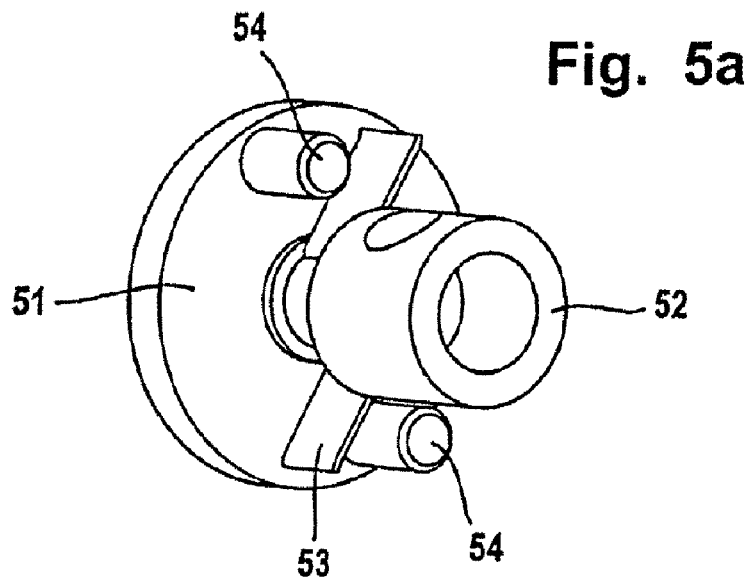
FIGS. 5a-5e are various views of a system with a torque-controlled clutch.
Figure 5B:
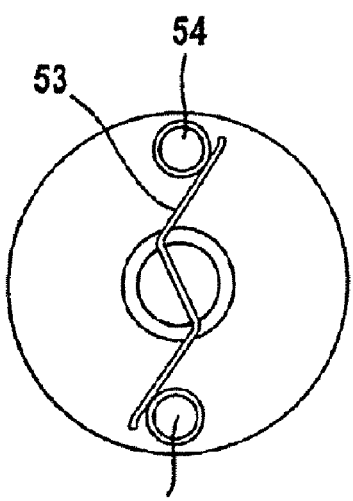
Figure 5C:
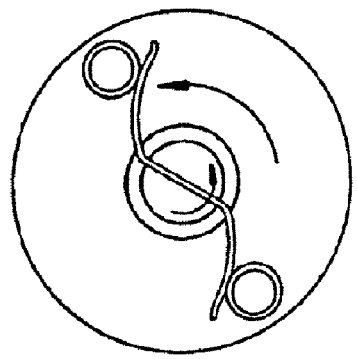
Figure 5D:
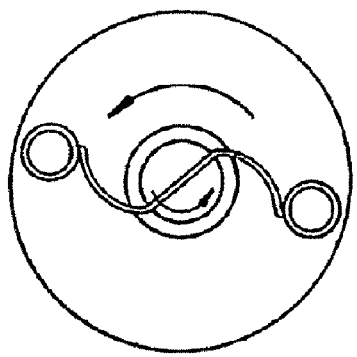
Figure 5E:
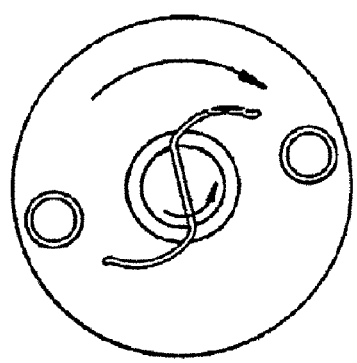
Figure 5F:
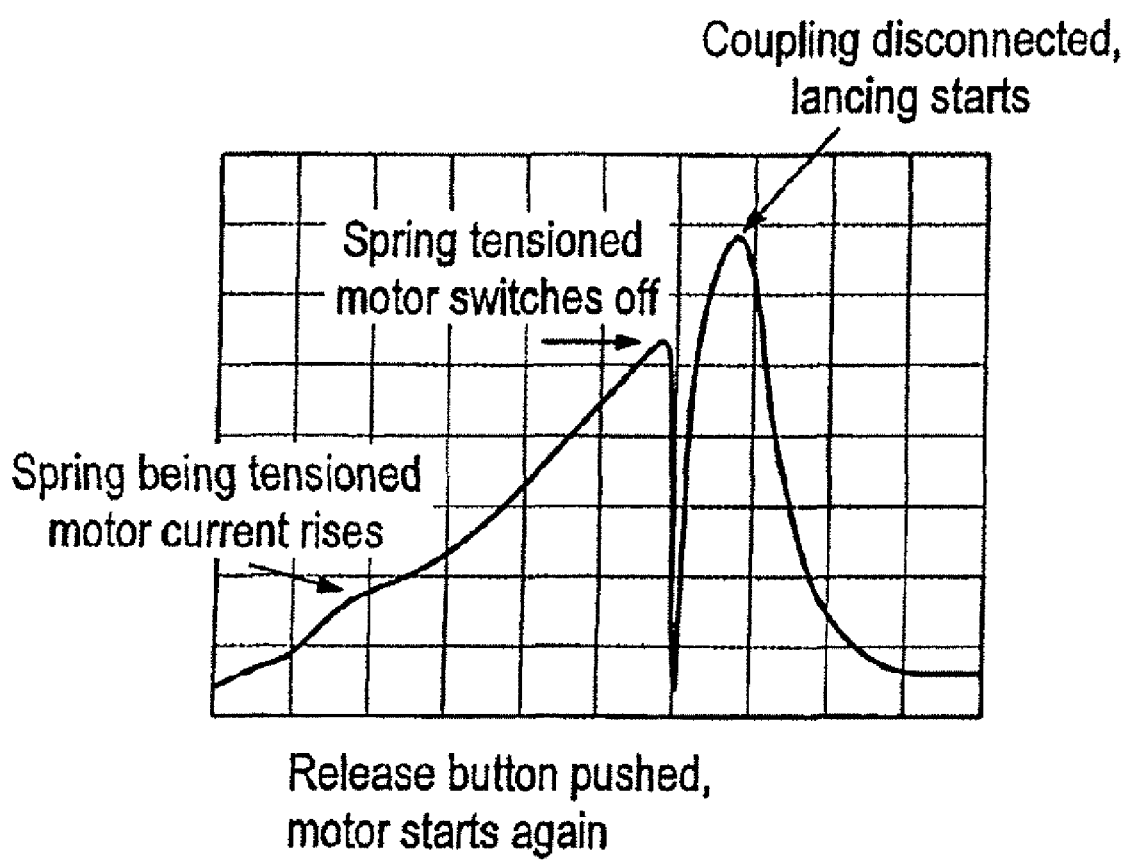
FIG. 5f is a graph of applied torque versus time.

FIGS. 5a-5e show a torque-controlled clutch which is also used as the coupling mechanism between the motor and a spring. The torque-controlled clutch consists of a first drive element 52 which has a leaf spring 53. Another drive element 51 with pins 54 is rotatably connected to the drive element 52. As shown in FIGS. 5a-5d, the spring is tensioned by first rotating the drive element 51 by means of a motor (not shown) while the drive element 52 remains stationary in the system. As a result the leaf spring 53 is pressed against the pins 54 and is thus bent. As the angle of rotation increases, the torque increases and thus the motor current necessary to tension the spring increases, as illustrated in the graph FIG. 5f. The motor current is measured by drive electronics (not shown) and is compared with a set limit value. When a first specified limit is reached, the motor is stopped. The spring is now completely tensioned (see FIG. 5d). The motor is again switched on to trigger the lancing process. The torque increases again. When the trigger point of a second given limit value of the clutch is reached which is larger than the first set limit value, the form-locking connection between the leaf spring 53 and the pins 54 is released and the spring can run back in an almost frictionless manner. The released energy is converted in order to execute a lancing movement (see FIG. 5e). The applied torque decreases back to almost zero as shown in FIG. 5f.

FIGS. 6-8 show several embodiments of a coupling in which a rotating mass is used as a mechanical energy store. In this manner the energy required for a lancing process is stored in the form of kinetic energy and is subsequently provided for a lancing process. When a mass is used as a mechanical energy store it is possible to, among other things, omit gearing and/or clutch to couple the motor to the mechanical energy store. This simplifies the design of the system compared to a design which has a spring as a mechanical energy store. The structure of the drive unit can also be reduced in size. If a moving mass is used as a mechanical energy store, it is thus possible to directly connect an electric motor to the mass to be accelerated and to rotate the mass. In this way kinetic energy is first stored by a simple type of construction. However, the stored energy must be rapidly transferred from the energy store to the lancet body with little loss. Such an energy transfer can take place by means of a suitable clutch between the mechanical energy store, in this case the moving mass, and the lancet. This coupling should operate with as little loss as possible and have short response times to minimize energy losses due to friction. In principle, two advantageous embodiments are possible which allow transfer of energy to the lancet body in a rapid and low-loss manner. On the one hand, the kinetic energy can be directly transferred onto the lancet body or onto a mechanical motion converter and thus into a lancing process. It is, however, also possible that the energy of rotation is first transferred onto a further intermediate store which is for example in the form of a spring. This has the advantage that when a lancing process is triggered, the mass does not at first have to be rotated to provide the necessary energy for the lancing process. The consequence of such a mechanism would be that after triggering the lancing process, the user would have to wait a few seconds until the mass has been suitably accelerated by the electric motor and energy transfer can subsequently take place. If, however, an intermediate store is used in conjunction with the rotating mass, it is possible to first temporarily store the energy obtained by rotation in a spring. The lancing process can then be triggered at any time and directly by, for example, relaxing a compressed spring as an intermediate store and is implemented similarly to the systems already described above in which a spring is used as a mechanical energy store. Consequently, if a rotating mass is used in combination with an intermediate store, the user is provided with the same methods of handling the system already described. Thus, in this example the rotating mass is an alternative solution for tensioning a spring without requiring appropriate gearing and/or clutches to connect the motor and energy store. Thus, tensioning a spring, which would otherwise require high torque, is possible by a direct transfer of the kinetic energy onto the spring. In general a coupling between the mass and an intermediate store or a lancet body enables the kinetic energy to be transferred suddenly in about 1 ms. This allows either a direct conversion of rotational energy into a lancing movement or an efficient storage of energy in an intermediate store despite a simple design of the system.

Figure 6A:
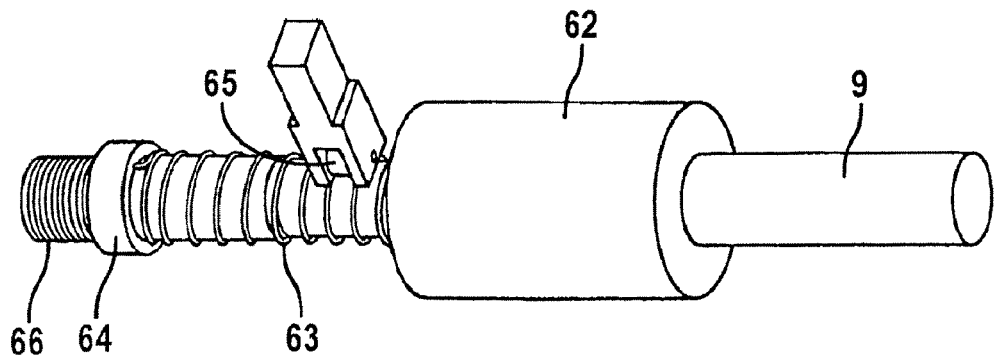
FIGS. 6a-6c are various views of one embodiment of a system with a rotating mass used as a mechanical energy store.
Figure 6B:
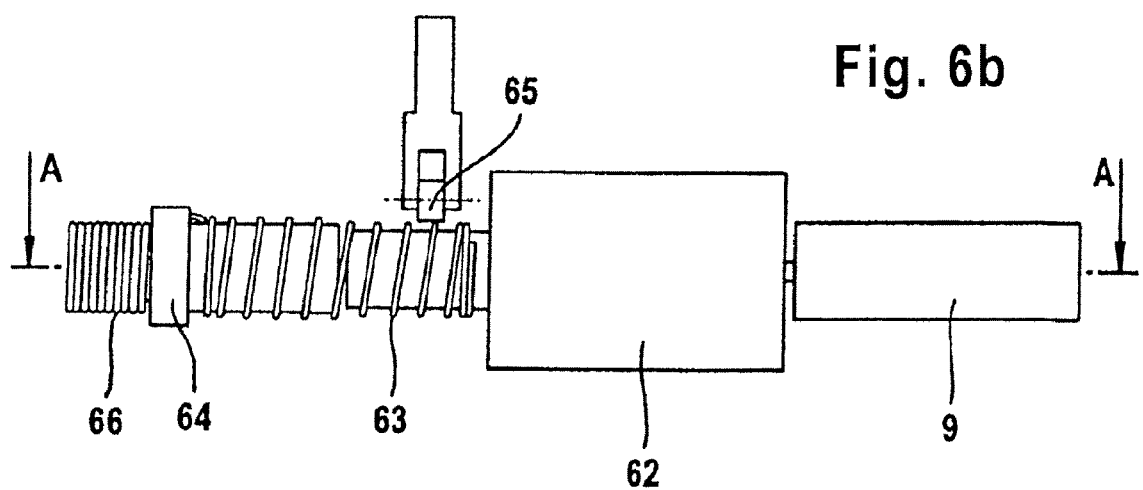
Figure 6C:
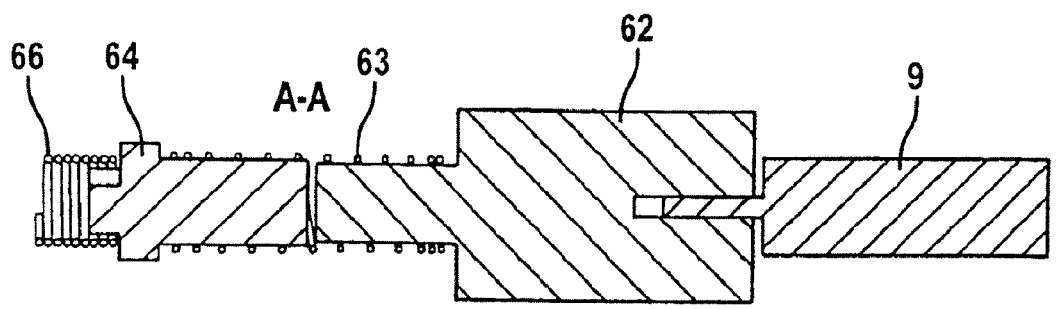
Figure 8A:
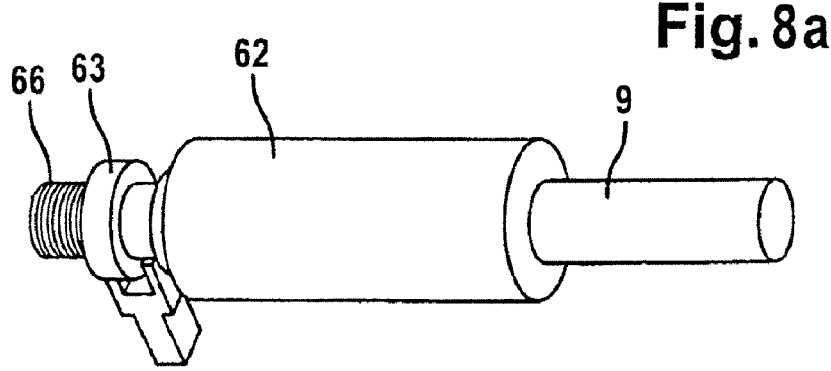
Figure 8B:
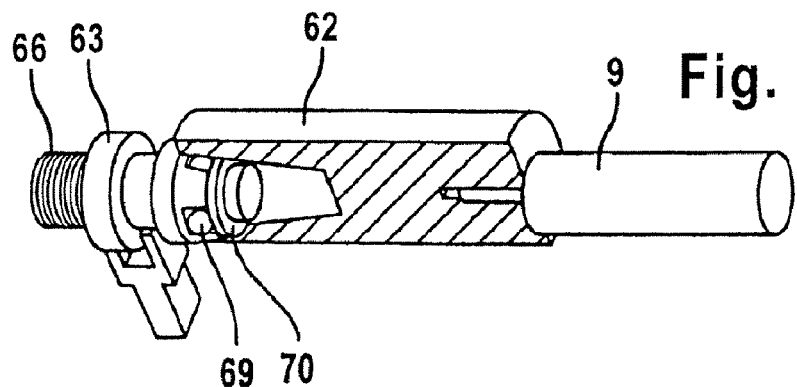
Figure 8C:
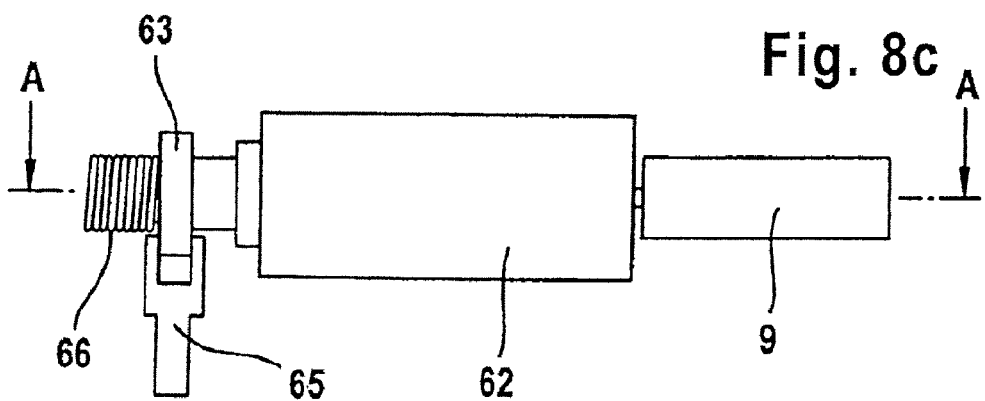
Figure 8E:
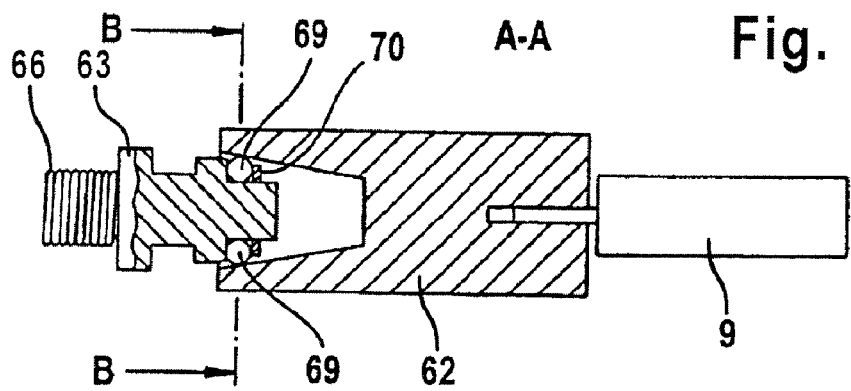
Figure 8E:
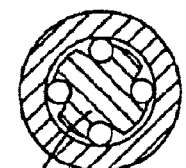

FIGS. 6a-6c show an electric motor 9 which is connected to a mass 62 in order to accelerate the mass and to rotate it. The windings of a wrap spring 63 are pressed onto the pin of the rotation mass 62 by pressing the switch button 65. If the mass is driven by the motor, the spring 63 is thereby abruptly wound onto the pin which accelerates the spindle 64. Depending on the drive principle that is used, the rotary movement of the spindle 64 is used to tension the drive spring 66 which is used as an intermediate store, or is directly converted into the lancing movement. Thus, the lancing process can be directly triggered by pressing the switch button 65. If, however, an intermediate store 66 is used, the kinetic energy is first temporarily stored by automatically actuating the switch button and the spring 66 is thereby compressed. The spring is subsequently relaxed by a separate triggering process for the intermediate store, by which means a lancet body can be propelled. In order to simplify the release of a wrap spring 63 that may have become jammed, the motor can be briefly turned in the opposite direction after carrying out the tensioning or lancing process. In principle, the process steps necessary for the lancing process can be automated so that the switch 65 is automatically actuated when a preset rotational frequency is reached. Furthermore, the release of the wrap spring and thus the actuation of the motor in the opposite direction can be initiated automatically after completion of the lancing process. However, it is often desirable that the lancing process is triggered consciously by the user.

FIGS. 7a-7e show another principle with a frictional directional lock which enables the kinetic energy of a rotating mass to be transferred onto a lancet body. Like in the embodiment in FIGS. 6a-6c, the mechanical energy store in the embodiment in FIGS. 7a-7e first has an electric motor 9 which accelerates a mass 62. The frictional directional lock 67 is axially displaced by sliding a switch 65. As a result, the clamping arms of the frictional directional lock 67 are pressed against the outer wall of the cone of the rotating mass 62. Once the clamping arms are locked with the mass 62, the frictional directional lock is abruptly accelerated and follows the course of movement of the rotation mass 62. Similar to the embodiments described above, the drive mechanism can be directly coupled to the lancet body or to an intermediate store. The frictional directional lock 67 is pulled out of the cone of the rotation mass 62 by sliding the switch 65 in order to release the coupling connection and thus the locking connection between the frictional directional lock 67 and the rotation mass 62.

FIGS. 8a-8e show a further embodiment for coupling a rotating mass to a lancet body or to an intermediate store as already presented in FIGS. 6 and 7. Similar to the embodiments described above, the system has an electric motor 9 which accelerates the rotation of a mass 62. The freewheeling spindle 68 is abruptly coupled to the rotation mass 62 by sliding a switch 65 such that the kinetic energy of the mass 62 can be transferred to the lancet body or to an intermediate store as free from loss and as directly as possible. For this purpose, the system has a number of locking balls 69 which, similar to the principle presented in FIGS. 7a-7e, are locked with the cone of the rotation mass by sliding the switch. In this case, holding disks 70 prevent the balls 69 from falling out, such that the balls couple the spindle 63 to the rotation mass 62. In this manner, the freewheeling spindle 68 is forced to follow the movement of the rotation mass 62, whereby the energy is transferred within a millisecond from the rotation mass onto the spindle 69. Also, in this case, the spindle 64 is pulled out of the cone of the mass to detach the coupling connection by sliding the switch 65, which disconnects the spindle 64 and rotation mass 62.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A device for acquiring and analyzing a sample fluid, comprising:
   a housing having an opening;
   a lancet having a lancet body movably disposed in the housing;
   a drive unit configured to propel the lancet body such that the tip of the lancet can at least partially protrude from the opening to perform a lancing process, the drive unit comprising:
      a motor configured for contact with an electrical energy store;
      a mechanical energy store coupled to the motor such that the electrical energy stored by the electrical energy store can be converted into mechanical energy and at least partially stored by the mechanical energy store; and a coupling mechanism which couples the lancet body to the mechanical energy store, wherein the stored energy of the mechanical energy store can be at least partially transferred to the lancet body, the coupling mechanism comprising a mechanical motion converter which diverts the energy of the mechanical energy store onto the lancet body to move the lancet in a positively guided movement, the mechanical motion converter comprising a control guide block which is configured to guide the movement of the lancet; and the motor being coupled to a functional component which is independent of the mechanical energy store, wherein the energy from the motor is configured to be diverted to the mechanical energy store and the functional component.

2. The device of claim 1, wherein the mechanical energy store is integrated as a solid body in the device.

3. The device of claim 2, wherein the mechanical energy store is a spring.

4. The device of claim 2, wherein the mechanical energy store is a mass.

5. The device of claim 1, wherein the mechanical motion converter has a cross-slip gear unit.

6. The device of claim 1, wherein the motor has a gear unit which couples the motor to the mechanical energy store.

7. The device of claim 6, wherein the gear unit is a bevel gearing.

8. The device of claim 1, wherein the motor has a clutch which couples the motor to the mechanical energy store.

9. The device of claim 8, wherein the motor is controlled as a function of current.

10. The device of claim 8, wherein the clutch transfers a torque of at least 10 mNm to the mechanical energy store.

11. The device of claim 8, wherein the clutch is controlled by torque or angle of rotation.

12. The device of claim 1, wherein the coupling mechanism comprises a clutch.

13. The device of claim 1, wherein the electric motor comprises a piezoelectric motor or an external rotor motor.

14. The device of claim 1, wherein the energy for the mechanical energy store and the energy for the functional component that is independent of the energy store are provided simultaneously or independently of one another.

15. The device of claim 1, wherein the functional component that is independent of the energy store is a test element transport or a magazine transport.

16. The device of claim 1, wherein several test elements are stored in a magazine in the device.

17. A device for obtaining and analyzing a body fluid sample, comprising:
a housing;
a lancet body movably disposed in the housing, the lancet body defining a lancet having a tip;
a motor;
a mechanical energy store coupled to the motor, wherein energy from the motor is configured to be transferred to and stored by the mechanical energy store, the mechanical energy store being configured to release the stored energy to move the lancet body in a puncturing motion;
a control guide block which is configured to guide the movement of the lancet; and
an auxiliary functional component coupled to the motor, wherein additional energy from the motor is configured to be transferred to and used by the auxiliary functional component, wherein the energy from the motor is configured to be diverted to the mechanical energy store and the auxiliary functional component.

18. The device of claim 17, wherein the auxiliary functional component comprises a test element transport or a magazine transport.

19. The device of claim 17, wherein the auxiliary functional component comprises a magazine transport, the device further comprising a magazine in which several test elements are stored.

20. The device of claim 19, wherein the magazine is rotatably disposed in the housing.

21. The device of claim 17, wherein the motor is controlled as a function of current.

22. The device of claim 17, wherein the mechanical energy store comprises a spring which is tensioned by the motor.

23. The device of claim 17, wherein the mechanical energy store comprises a rotating mass that is rotated by the motor.

24. The device of claim 17, wherein the motor has a clutch which couples the motor to the mechanical energy store.

25. A method of operating an integrated testing device of the type having a lancet drive with a lancet for puncturing skin and a transport for transporting test elements, the method comprising:
providing a mechanical energy store configured to drive the lancet drive;
coupling a motor to the mechanical energy store and to the transport;
transferring energy from the motor to advance the transport and to the mechanical energy store, the energy transferred to the mechanical energy store being at least partially stored; and
releasing the stored energy of the mechanical energy store through a controlled guide block to the lancet to drive the lancet in a positively guided puncturing movement.

26. The method of claim 25, wherein the step of advancing the transport comprises advancing a test tape.

27. The method of claim 25, wherein the step of advancing the transport comprises rotating a magazine containing test elements.

28. The method of claim 25, further comprising providing a clutch operable to transfer energy from the motor to the mechanical energy store or to transfer energy from the mechanical energy store to the lancet body.

29. A device for obtaining and analyzing a body fluid sample, comprising:
a housing;
a lancet body movably disposed in the housing, the lancet body defining a lancet having a tip;
a motor;
a mechanical energy store coupled to the motor, wherein energy from the motor is configured to be transferred to and stored by the mechanical energy store, the mechanical energy store being configured to release the stored energy to move the lancet body in a puncturing motion;
an auxiliary functional component coupled to the motor, wherein additional energy from the motor is configured to be transferred to and used by the auxiliary functional component, wherein the energy from the motor is configured to be diverted to the mechanical energy store and the auxiliary functional component; and
a clutch operable to transfer energy from the motor to the mechanical energy store or to transfer energy from the mechanical energy store to the lancet body.

30. The device of claim 29, wherein the clutch couples the motor to the mechanical energy store.

31. The device of claim 29, wherein the clutch couples the mechanical energy store to the lancet body.

32. The device of claim 29, wherein the mechanical energy store comprises a solid body in the device.

33. The device of claim 32, wherein the mechanical energy store comprises a spring.

34. The device of claim 32, wherein the mechanical energy store comprises a mass.

35. The device of claim 29, wherein the motor is controlled as a function of current.

36. The device of claim 29, wherein the clutch transfers a torque of at least 10 mNm to the mechanical energy store.

37. The device of claim 29, wherein the clutch is controlled by torque or angle of rotation.

38. The device of claim 29, wherein the energy for the mechanical energy store and the energy for the auxiliary functional component are provided simultaneously.

39. The device of claim 29, wherein the energy for the mechanical energy store and the energy for the auxiliary functional are provided independently.

* * * * *